(12) United States Patent
Komuro

(10) Patent No.: US 8,562,533 B2
(45) Date of Patent: Oct. 22, 2013

(54) ULTRASOUND OBSERVATION APPARATUS

(75) Inventor: Masahiko Komuro, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/536,319

(22) Filed: Jun. 28, 2012

(65) Prior Publication Data

US 2012/0271172 A1    Oct. 25, 2012

Related U.S. Application Data

(63) Continuation of application No. PCT/JP2011/076391, filed on Nov. 16, 2011.

(30) Foreign Application Priority Data

Dec. 28, 2010   (JP) .................................. 2010-293550

(51) Int. Cl.
*A61B 8/00*        (2006.01)
(52) U.S. Cl.
USPC ......................................... 600/441; 600/440
(58) Field of Classification Search
USPC .................. 600/437, 440, 441, 459; 310/322; 367/138, 181
See application file for complete search history.

(56) References Cited

U.S. PATENT DOCUMENTS

| 6,795,374 B2 | 9/2004 | Barnes et al. |
| 2003/0048698 A1 | 3/2003 | Barnes et al. |
| 2008/0064959 A1 | 3/2008 | Kanda et al. |
| 2009/0079299 A1 | 3/2009 | Bradley et al. |
| 2010/0278015 A1 | 11/2010 | Huang |

FOREIGN PATENT DOCUMENTS

| JP | 10-033533 | 2/1998 |
| JP | 2006-122344 | 5/2006 |
| JP | 2009-239976 | 10/2009 |
| JP | 2010-540071 | 12/2010 |
| WO | WO 2006/041114 A1 | 4/2006 |
| WO | WO 2009/042027 A1 | 4/2009 |

OTHER PUBLICATIONS

European Search Report dated Dec. 17, 2012 from corresponding European Patent Application No. EP 11 85 2859.5.

*Primary Examiner* — Michael Rozanski
(74) *Attorney, Agent, or Firm* — Scully, Scott, Murphy & Presser, P.C.

(57) ABSTRACT

An ultrasound observation apparatus to which an ultrasound probe is connectable, the ultrasound probe including a capacitive micromachined ultrasound transducer whose sensitivity can be controlled according to an applied bias voltage, the ultrasound observation apparatus including a transmit section that outputs a transmit signal for causing ultrasound to be transmitted; a receive section that performs signal processing on a received receive signal; a bias voltage outputting section that varies the applied bias voltage, an image mode setting section that designates and sets an image mode for displaying an ultrasound image corresponding to ultrasound scanning; a parameter setting section that designates and sets a parameter for signal processing performed by the transmit section or the receive section, and a control section that controls the bias voltage based on a designation signal corresponding to the designation and setting of the image mode and the parameter.

14 Claims, 8 Drawing Sheets

ULTRASOUND OBSERVATION APPARATUS

CROSS REFERENCE TO RELATED APPLICATION

This application is a continuation application of PCT/JP2011/076391 filed on Nov. 16, 2011 and claims benefit of Japanese Application No. 2010-293550 filed in Japan on Dec. 28, 2010, the entire contents of which are incorporated herein by this reference.

BACKGROUND OF THE INVENTION

1. Field of the Invention

The present invention relates to an ultrasound observation apparatus that generates an ultrasound image using capacitive micromachined ultrasound transducer(s).

2. Description of the Related Art

In recent years, ultrasound observation apparatuses or ultrasound diagnostic apparatuses capable of displaying an ultrasound image of, e.g., a diseased part in a body cavity using an ultrasound probe including ultrasound transducer(s) have widely been used.

Also, capacitive micromachined ultrasound transducers (referred to as C-MUTs) that can easily comply with RoHS, which is a directive issued by the European Union (EU) for restriction of the use of certain hazardous substances in electrical and electronic equipment, and has a broadband characteristic are drawing attention.

As a first related art example, for example, International Publication No. 2006/0411114 discloses an ultrasound observation apparatus in which a DC bias voltage for providing a reference sensitivity is applied during transmission and the DC bias voltage is variably controlled with time during reception. Hereinafter, since DC bias voltage varies depending on the time, the below description will be provided simply using "bias voltage".

Also, as a second related art example, Japanese Patent Application Laid-Open Publication No. 2006-122344 discloses an ultrasound observation apparatus in which a bias voltage is controlled to gradually increase from a near field to a far field in a receive period.

Furthermore, as a third related art example, U.S. Pat. No. 6,795,374 discloses that a bias voltage is variably controlled according to a function of an image mode according to ultrasound scanning

SUMMARY OF THE INVENTION

An ultrasound observation apparatus according to an aspect of the present invention includes an ultrasound observation apparatus to which an ultrasound probe is connectable, the ultrasound probe including a capacitive micromachined ultrasound transducer whose sensitivity can be controlled according to an applied bias voltage, the ultrasound observation apparatus including: a transmit section that performs signal processing for outputting a transmit signal for causing the capacitive micromachined ultrasound transducer to transmit ultrasound, to the capacitive micromachined ultrasound transducer; a receive section that performs signal processing on a receive signal received by the capacitive micromachined ultrasound transducer, to display the receive signal as an ultrasound image; a bias voltage outputting section that variably outputs the bias voltage applied to the capacitive micromachined ultrasound transducer; an image mode setting section that designates and sets an image mode for displaying an ultrasound image corresponding to ultrasound scanning by the capacitive micromachined ultrasound transducer; a parameter setting section that designates and sets a parameter for the signal processing on the transmit signal or the received receive signal; an operation section including the image mode setting section and the parameter setting section, the operation section outputting a designation signal corresponding to the designation and setting of the image mode and the parameter; and a control section that controls the bias voltage based on the designation signal from the operation section, wherein the image mode setting section designates and sets a B-mode for imaging and displaying a luminance corresponding to a position and an amplitude of the receive signal or a Doppler mode for providing display as a Doppler image using a Doppler phenomenon; wherein the parameter setting section designates and sets at least one of a gain for the receive signal, a display range for which the ultrasound image is displayed, a focal length for the ultrasound transmitted from the capacitive micromachined ultrasound transducer to be focused, a wavenumber of the transmit signal when the transmit signal is transmitted in the Doppler mode, a scanning type of the ultrasound probe, a number of elements of the capacitive micromachined ultrasound transducers simultaneously driven if the ultrasound probe is an electronic scanning one, as a parameter; and wherein the control section controls the bias voltage in synchronization with the transmit signal and according to the designation and setting of image mode designated by the image mode setting section and the parameter by the parameter setting section; and wherein the control section controls the bias voltage so that the bias voltage has a constant value in a receive period in which a distance from the capacitive micromachined ultrasound transducer varies from a near field to a far field if the Doppler mode is designated and set, and variably controls a value of the bias voltage in the receive period so as to increase the value as the distance varies from the near field to the far field if the B-mode is designated and set by the image mode setting section.

DETAILED DESCRIPTION OF THE PREFERRED EMBODIMENTS

Hereinafter, embodiments of the present invention will be described with reference to the drawings.
(First Embodiment)

Figure 1:
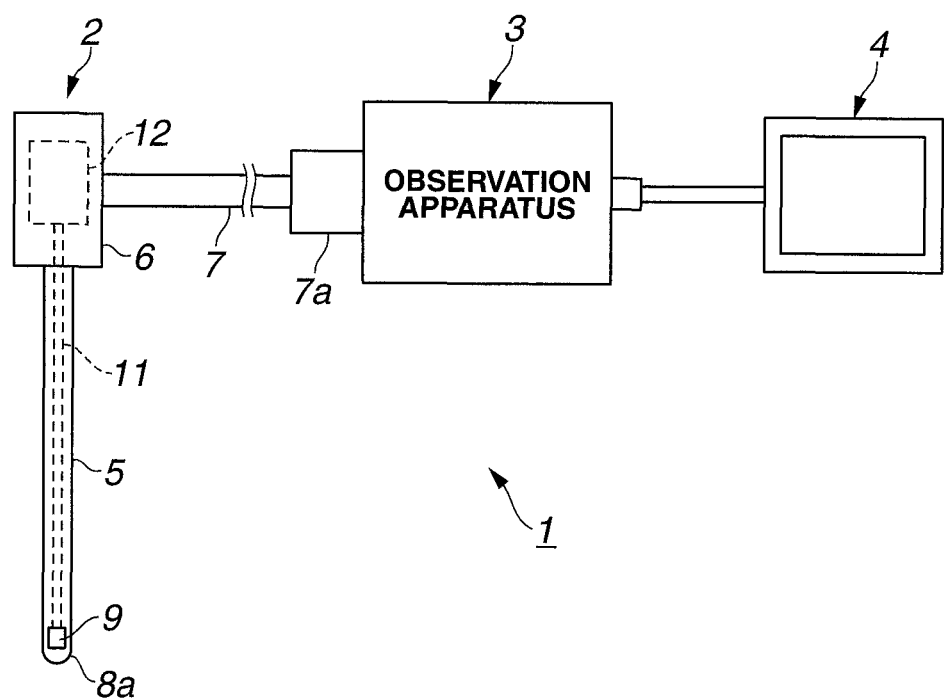
FIG. 1 is a diagram illustrating an entirety of an ultrasound diagnostic apparatus including a first embodiment of the present invention.

As illustrated in FIG. 1, an ultrasound diagnostic apparatus 1 including a first embodiment of the present invention includes a mechanical scanning ultrasound probe 2 to be inserted into, e.g., a body cavity, an ultrasound observation apparatus 3 to which the ultrasound probe 2 is detachably connected (hereinafter simply referred to as "observation apparatus"), and a monitor 4 that displays an ultrasound image.

The ultrasound probe 2 includes an elongated insertion portion 5 to be inserted into, e.g., a body cavity, a grasping portion 6 provided at a rear end of the insertion portion 5, the grasping portion 6 being grasped by an operator, such as a surgeon, and a cable portion 7 extending from the grasping portion 6, and at an end portion of the cable portion 7, a connector 7a detachably connected to a connector receiver 8a (see FIG. 2) of the observation apparatus 3 is provided.

Inside a distal end portion 5a of the insertion portion 5, a capacitive micromachined ultrasound transducer (hereinafter abbreviated as "C-MUT") 9 whose sensitivity can be controlled according to an applied direct-current (DC) bias voltage is disposed. The C-MUT 9 is attached to a distal end of a flexible hollow shaft 11 inserted through the inside of the insertion portion 5, and a rear end of the hollow shaft 11 is connected to a rotation drive section 12 provided inside the grasping portion 6, the rotation drive section 12 being driven to rotate.

Figure 2:
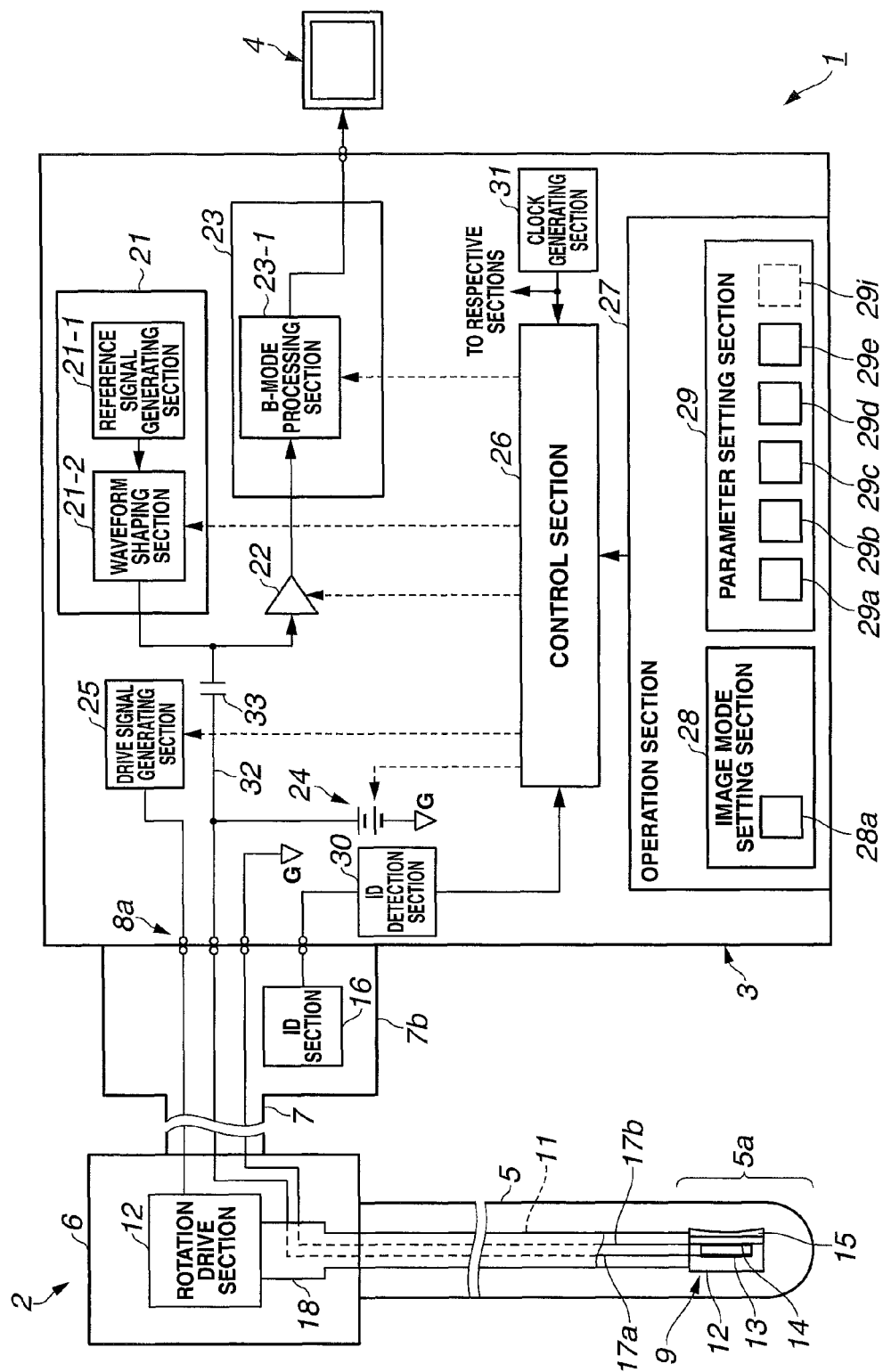
FIG. 2 is a diagram illustrating inner configurations of an ultrasound probe and an ultrasound observation apparatus in FIG. 1.

As illustrated in FIG. 2, the C-MUT 9 includes a hollow formed using, for example, silicon substrates, two substrate surfaces facing the hollow are provided with respective electrodes 13 and 14, and a film that vibrates by means of an static electric force between the electrodes 13 and 14 is formed on one of the substrate surfaces, whereby such substrate surface serves as a transmit/receive surface that transmits and receives ultrasound.

Furthermore, an acoustic lens 15 is attached to the transmit/receive surface and ultrasound emitted from the transmit/receive surface is set to be focused at a predetermined distance from the C-MUT 9, that is, a focal length by the acoustic lens 15.

The focal length for focusing by the acoustic lens 15 is set according to the type of the ultrasound probe 2. Furthermore, in, for example, the connector 7a of an individual ultrasound probe 2, an ID section 16 is provided as an identification information generating section that generates identification information (ID) unique to the ultrasound probe 2.

With rotation of the rotation drive section 12, the hollow shaft 11 also rotates, and the C-MUT 9 attached to the distal end of the hollow shaft 11 also rotates, whereby the C-MUT 9 transmits ultrasound via the transmit/receive surface and the acoustic lens 15 radially with the hollow shaft 11 as a center axis of the rotation and receives the transmitted ultrasound. Thus, the ultrasound probe 2 in the present embodiment is a mechanical scanning ultrasound probe that performs radial ultrasound scanning by mechanically driving rotation of the C-MUT 9.

As illustrated in FIG. 2, in the vicinity of the rear end of the hollow shaft 11, a slip ring section 18 for electrically connecting rotatable contact points (rotor-side contact points) electrically connected to signal wires 17a and 17b (together with the C-MUT 9), the signal wires 17a and 17b being connected to the electrodes 13 and 14 of the C-MUT 9 and inserted in the hollow shaft, to non-rotatable contact points (stator-side contact points) is provided.

Also, as illustrated in FIG. 2, the observation apparatus 3 includes a transmit section 21 that performs signal processing for outputting a transmit signal for causing the C-MUT 9 to transmit ultrasound to the C-MUT 9, an amplifier 22 that amplifies an ultrasound echo signal, which is a receive signal generated as a result of reception by the C-MUT 9, and a receive section 23, which is a receive signal processing section that performs signal processing on the amplified receive signal to display the amplified receive signal as an ultrasound image. Here, although FIG. 2 indicates an example in which the receive section 23 does not include the amplifier 22, the receive section 23 may include the amplifier 22.

The observation apparatus 3 also includes a bias voltage outputting section 24 that outputs (or generates) a (unipolar) bias voltage, which is to be applied to the C-MUT 9 when ultrasound transmission/reception is performed using the C-MUT 9, and a drive signal generating section 25 that generates a rotation drive signal that electrically drives the rotation drive section 12.

Furthermore, the observation apparatus 3 includes a control section 26 that controls operations of the transmit section 21, the amplifier 22, the receive section 23, the bias voltage outputting section 24 and the drive signal generating section 25, an operation section 27 for an operator to designate and set (designate and input) an image mode corresponding to a scanning mode and parameters, and an ID detection section 30 that detects identification information (ID) unique to the ID section 16. A designation signal from the operation section 27 and an ID detection signal from the ID detection section 30 are inputted to the control section 26.

Furthermore, the observation apparatus 3 is provided with a clock generating section 31 that generates a reference clock signal, and the clock generating section 31 supplies the clock signal to the respective sections in the observation apparatus 3, such as the transmit section 21, the receive section 23, the drive signal generating section 25 and the control section 26, and the respective sections operate in synchronization with the clock signal.

The operation section 27 is provided with an image mode setting section 28 for designating and setting an image mode for displaying an ultrasound image according to a scanning mode, and a parameter setting section 29 for designating and setting various types of parameters such as a gain for a receive signal.

The image mode setting section 28 is provided with a B-mode setting section 28a for designating and setting a B-mode for imaging and displaying a luminance corresponding to a position and an amplification of a receive signal. In the present embodiment, the observation apparatus 3 is one for a mechanical scanning ultrasound probe 2, and thus, the image mode setting section 28 is provided with the B-mode setting section 28a only.

As described in the later-described second embodiment, an observation apparatus 3B employing electronic scanning includes a Doppler mode setting section 28b for designating and setting a Doppler mode for displaying an ultrasound image corresponding to a frequency varying (i.e., Doppler effect) part of receive signals from a moving part to be observed such as a blood part as a Doppler image, in addition to the B-mode setting section 28a.

The parameter setting section 29 is provided with a gain parameter setting section 29a, a display range parameter setting section 29b, a focal length parameter setting section 29c, a (transmit signal) wavenumber parameter setting section 29d and an ultrasound probe type parameter setting section 29e for directing and setting a gain provided by, e.g., the amplifier 22 for a receive signal, a display range, which is a range to display an ultrasound image, a focal length, which is a distance from the C-MUT 9 to a point where ultrasound transmitted from the C-MUT 9 is focused, the number of transmit pulse waves in a transmit signal, and the type of the ultrasound probe, respectively.

The control section 26 controls operations of the transmit section 21, the amplifier 22, the receive section 23, the bias voltage outputting section 24 and the drive signal generating section 25 in response to designation signals from the operation section 27. In this case, the control section 26 controls a bias voltage from the bias voltage outputting section 24 and a timing for outputting the bias voltage in synchronization with a timing for outputting a transmit signal and according to at least one image mode from the image mode setting section 28 and at least one parameter from the parameter setting section 29 in the operation section 27.

Also, the control section 26 acquires the type of the ultrasound probe 2 actually connected to the observation apparatus 3 (in other words, information on, e.g., the type of the C-MUT 9 mounted (included) in the ultrasound probe 2 and whether the ultrasound probe 2 is one for mechanical scanning or electronic scanning) from the unique identification information in the ID section 16 via the ID detection section 30.

Then, the control section 26 controls an operation of the drive signal generating section 25 and operations of the transmit section 21 and the receive section 23 according to the acquired information. More specifically, the control section 26 controls the bias voltage from the bias voltage outputting section 24 and the output timing according to the size of the C-MUT 9 mounted (included) in the ultrasound probe 2 and/or the ultrasound transmit/receive characteristics (i.e., the type of the C-MUT 9). Furthermore, in terms of whether the ultrasound probe 2 is one for mechanical scanning or electronic scanning, the control section 26 controls the bias voltage from the bias voltage outputting section 24 and the output timing according to, e.g., the size of the C-MUT.

One output terminal of the transmit section 21 is connected to the electrode 13 of the C-MUT 9 via a signal wire 32 in the observation apparatus 3 and the signal wire 17a in the ultrasound probe 2. The other output terminal of the transmit section 21 is connected to a ground (the illustration abbreviated). Also, the signal wire 17b connected to the other electrode 14 of the C-MUT 9 is connected to a ground G in the observation apparatus 3.

The signal wire 32 is connected to one output terminal of the bias voltage outputting section 24, and the other output terminal of the bias voltage outputting section 24 is connected to the ground G. A capacitor 33 that cuts the bias voltage is disposed at a position part way through the signal wire 32 connected to the one output terminal of the bias voltage outputting section 24, thereby preventing the bias voltage generated in the bias voltage outputting section 24 from being applied to the transmit section 21.

Furthermore, the signal wire 32 is connected to an input terminal of the amplifier 22 connected in parallel to the transmit section 21, and here, the capacitor 33 also prevents the bias voltage generated in the bias voltage outputting section 24 from being applied to the amplifier 22.

The transmit section 21 includes a reference signal generating section 21-1 that generates a continuous-wave (sinusoidal-wave) reference signal in synchronization with the clock signal from the clock generating section 31, and a waveform shaping section 21-2 that shapes a waveform of the reference signal to output the reference signal as a transmit signal having a burst waveform.

The waveform shaping section 21-2, which is formed using, e.g., a gate circuit, upon application of a control signal designating a gate width (or a wavenumber) from the control section 26, shapes a waveform of only a reference signal having a wavenumber corresponding to the gate width as a transmit signal and outputs the reference signal. In other words, the waveform shaping section 21-2 varies and adjusts the wavenumber of the transmit signal having a burst waveform (also referred to as a wavenumber of burst waves) according to the control signal from the control section 26.

Meanwhile, the receive section 23, to which an output signal from the amplifier 22 is inputted, includes a B-mode processing section 23-1 that generates a B-mode ultrasound image. The B-mode processing section 23-1 can also control processing such as contour enhancement according to a control signal from the control section 26.

The observation apparatus 3 having such configuration is an ultrasound observation apparatus to which the ultrasound probe 2 is connectable, the ultrasound probe 2 including the C-MUT 9, which is a capacitive micromachined ultrasound transducer whose sensitivity can be controlled according to an applied bias voltage, the observation apparatus 3 including: the transmit section 21 that performs signal processing for outputting a transmit signal for causing the capacitive micromachined ultrasound transducer to transmit ultrasound, to the capacitive micromachined ultrasound transducer, and the receive section 23 that performs signal processing on a receive signal received by the capacitive micromachined ultrasound transducer, to display the receive signal as an ultrasound image.

The observation apparatus 3 also includes the bias voltage outputting section 24 that variably outputs the bias voltage applied to the capacitive micromachined ultrasound transducer, the image mode setting section 28 that designates and sets an image mode for displaying an ultrasound image according to a scanning mode of the capacitive micromachined ultrasound transducer, and the parameter setting section 29 that designates and sets a parameter for the signal processing on the transmit signal or the received receive signal.

The observation apparatus 3 further includes the operation section 27 including the image mode setting section 28 and the parameter setting section 29, the operation section 27 outputting a designation signal corresponding to the designation and setting of the image mode and the parameter, and the control section 26 that controls the bias voltage based on the designation signal from the operation section 27.

Next, an operation according to the present embodiment will be described. An operator such as a surgeon connects the ultrasound probe 2 to the observation apparatus 3 and also connects the monitor 4, which is means for displaying an ultrasound image, to the observation apparatus 3 as illustrated in FIG. 2.

Then, the operator such as a surgeon inserts the ultrasound probe 2 into a body cavity of a patient, and superimposes a transmit signal from the transmit section 21 on a bias voltage and applies the bias voltage with the transmit signal superimposed thereon to the C-MUT 9 included in the ultrasound probe 2, thereby transmitting ultrasound from the C-MUT 9 toward the inside of the body cavity.

In this case, the operator normally designates and sets the B-mode as an image mode via the image mode setting section 28. Where the image mode of the B-mode is designated and set, the control section 26 performs control so that the transmit section 21 outputs a transmit signal having a wavenumber of, for example, one, as illustrated in FIG. 3(A).

Also, where the operator designates and sets a small gain or a large gain via (the gain parameter setting section 29a in) the parameter setting section 29, the control section 26 controls the bias voltage according to the designation and setting as FIGS. 3(B) or 3(C), respectively.

The control section 26 also controls a gain value of the amplifier 22 according to the designation and setting of a small gain or a large gain.

Figure 3:
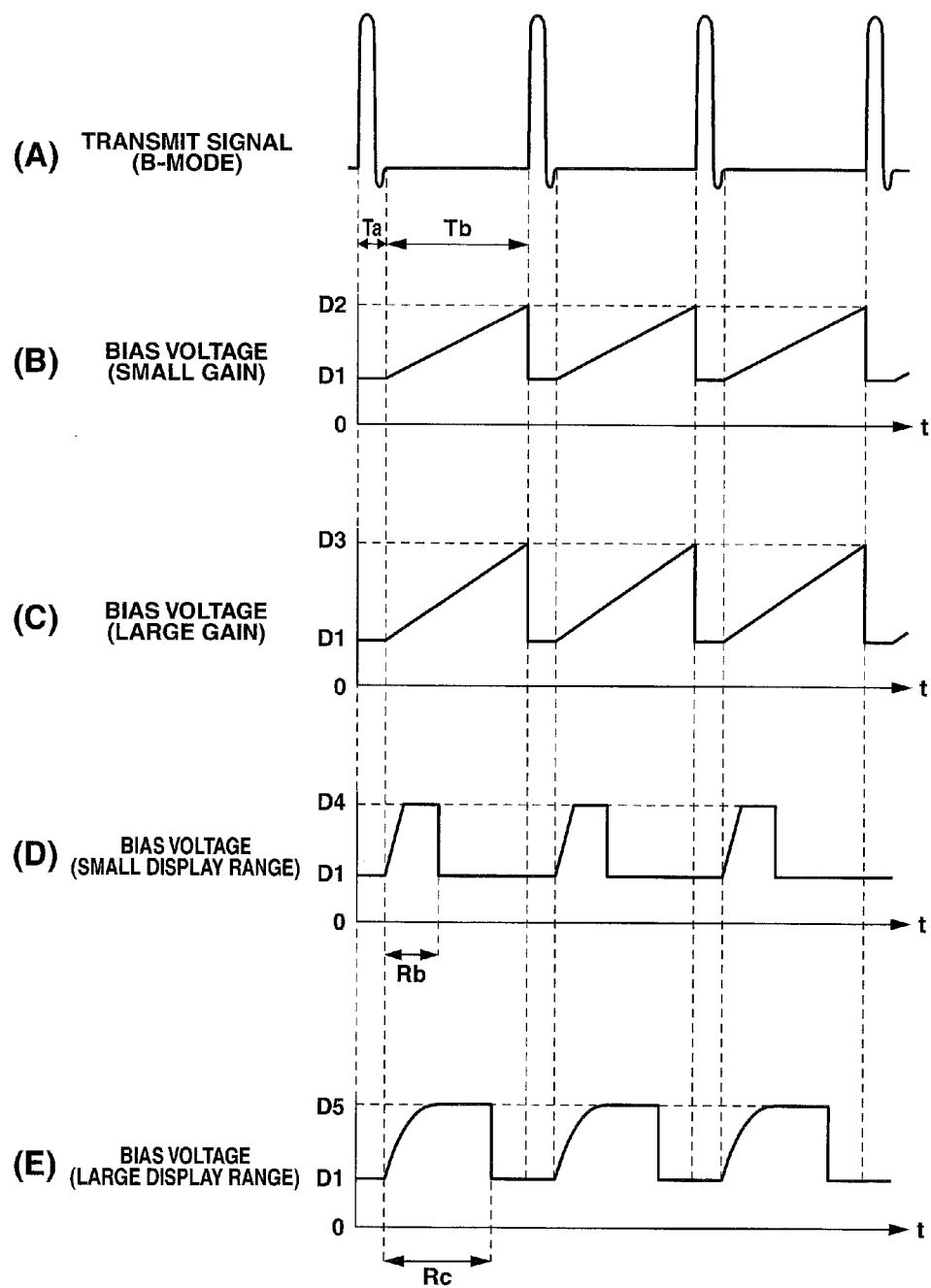
FIG. 3 includes diagrams illustrating example waveforms of bias voltages set in synchronization with a transmit signal and according to gains and display ranges.
Figure 4:
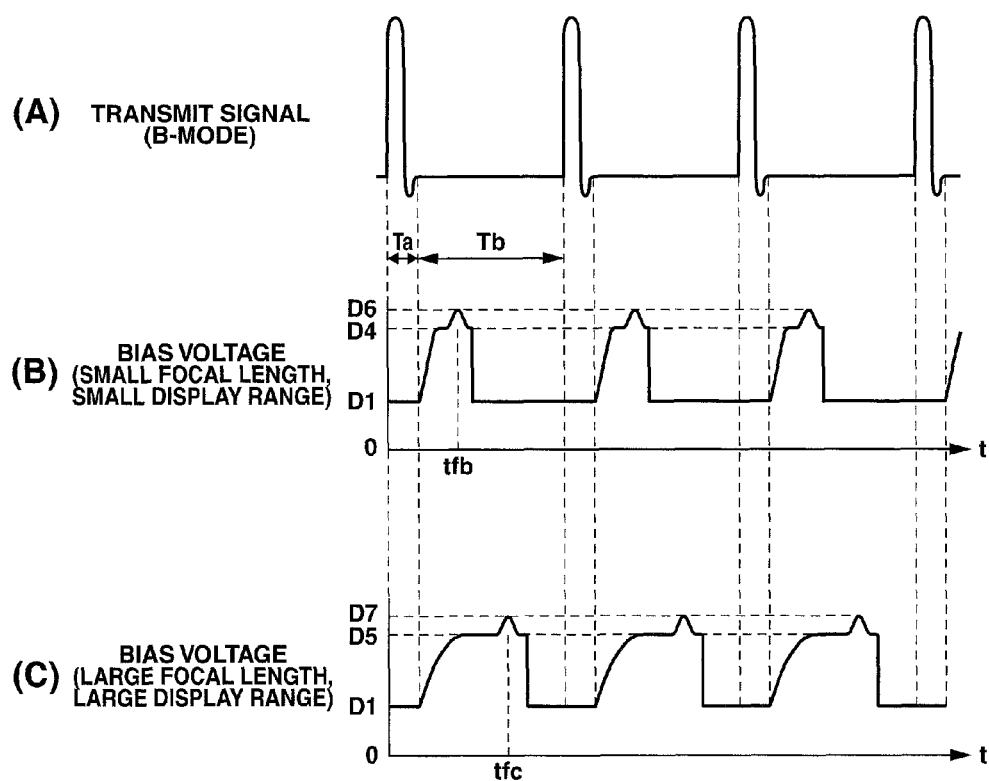
FIG. 4 includes diagrams illustrating example waveforms of bias voltages set in synchronization with a transmit signal and according to focal lengths.

The control section 26 controls a value and a timing of the bias voltage so that the bias voltage outputting section 24 outputs the bias voltage as illustrated in FIG. 3 (B) or FIG. 3 (C), in synchronization with the transmit signal. The abscissa axes in FIG. 3 indicate passage of time, and the ordinate axis in FIG. 3(A) indicates amplitude, and the ordinate axes in FIGS. 3(B) and 3(C) indicate voltage level. Reference numeral Ta denotes a transmit period of the transmit section 21, and after the transmit period Ta, a receive period Tb in which the amplifier 22 and the receive section 23 receive ultrasound comes. The same applies to another figure, FIG. 4. The receive period Tb after the transmit period Ta corresponds to a distance to a tissue to be observed from which the C-MUT 9 receives a receive signal.

As can be seen from FIGS. 3(B) and 3(C), during transmission (transmit period Ta), the bias voltage is small (for example, D1). Meanwhile, during reception (receive period Tb), control is performed (the control section 26 controls the bias voltage outputting section 24) so that as the designated and set gain is larger, a peak value (maximum value) of the bias voltage increases. In the illustrated example, in the case of a gain designated and set to be small, the peak value of the bias voltage is D2, and in the case of a gain designated and set to be large, the peak value of the bias voltage is set to be D3 (>D2), which is larger than D2.

As a result of the control described above, where the operator designates and sets a large gain or a small gain, the bias voltage during reception is variably controlled according to the designation and setting. For example, where the operator designates and sets a larger gain, the value of the bias voltage during reception is made to be larger to enhance the sensitivity of the C-MUT 9 to a receive signal.

Accordingly, more effective sensitivity adjustment can be made compared to sensitivity adjustment using the amplifier 22 alone, and variable control of the bias voltage more properly responding to the designation and setting made by the operator can be performed. Furthermore, an ultrasound image more properly responding to the designation and setting made by the operator can be generated. In the above example, an ultrasound image more properly responding to the designation and setting of a gain made by the operator can be generated.

Where the gain is increased by the amplifier 22, noise in a receive signal inputted to the amplifier 22 is also increased accompanying the receive signal, resulting in difficulty in S/N ratio improvement. Meanwhile, where the bias voltage for the C-MUT 9 is increased, the sensitivity of the C-MUT 9 increases, providing the advantage of S/N ratio improvement compared to the case where the gain is increased by the amplifier 22. Thus, an ultrasound image having a favorable image quality and a good S/N ratio can be generated even when the gain is increased.

Where the operator designates and sets a large or small display range via (the display range parameter setting section 29b in) the parameter setting section 29, the control section 26 controls the bias voltage as indicated in FIG. 3(D) or FIG. 3(E), respectively, in response to the designation and setting.

As can be seen from FIGS. 3(D) and 3(E), the control section 26 performs control so that the bias voltage is large during a receive period Rb or Rc corresponding to the designated and set display range and the bias voltage is small during the receive period Tb except the receive period Rb or Rc.

As a result of the control being performed so that the bias voltage is large only during the receive period Rb or Rc corresponding to a display range for actually displaying an ultrasound image as described above, it is possible to make setting so as to acquire an ultrasound image having a favorable image quality with a required sensitivity maintained for the display range and reduce the bias voltage during the receive period Tb, which is not used for display, to achieve power saving.

Although in the illustrated example, peak values D4 and D5 of the bias voltage for the receive periods Rb and Rc corresponding to the display range are indicated as D4=D5, different values may be set. Also, the bias voltage may be variably set to have a pulse shape so that the bias voltage has the peak value D4 or D5 throughout the receive period Rb or Rc.

Furthermore, where the operator designates and sets a focal length via (the focal length parameter setting section 29c in) the parameter setting section 29, the control section 26 controls the bias voltage as illustrated in FIG. 4(B) or 4(C) according to the designation and setting. Here, FIG. 4(A) indicates a transmit signal as in FIG. 3(A).

Although in the present embodiment, a focal length of the acoustic lens 15 in the ultrasound probe 2 actually connected to the observation apparatus 3 can be designated and set via the focal length parameter setting section 29c, the focal length of the acoustic lens 15 can also be designated and set using the ID detection section 30.

Where the focal length of the acoustic lens 15 is designated and set using the ID detection section 30, for example, the operator makes a selection to turn on a focal length parameter (from ON/OFF in automatic detection) via the focal length parameter setting section 29c. Consequently, the control section 26 detects a value of the focal length of the acoustic lens 15 of the ultrasound probe 2 corresponding to the ID detected by the ID detection section 30 in ID detection. Then, using the value of the focal length, the control section 26 performs control similar to that of the case where the focal length parameter is designated and set.

FIGS. 4(B) and 4(C) indicate waveforms of the bias voltage in a case where the display range is designated and set to be small as in FIG. 3(D) and a case where the display range is designated and set to be large as in FIG. 3(E), for example, respectively. Around a receive signal time tfb (or tfc) corresponding to a position of the focal length, the bias voltage is set so as to have a value D6 (or D7) larger than a value D4 (or D5) before and after that time (that is, D6>D4 and D7>D5).

Accordingly, around the focal length, an ultrasound image with a favorable image quality whose sensitivity is increased around the focal length can be acquired.

Although FIGS. 4(B) and 4(C) indicate examples where the value D6 and D7 of the bias voltage around the receive signal times tfb and tfc corresponding to positions of the focal length are larger than the values of the bias voltage indicated in FIG. 3(D) and 3(E), respectively, it is possible to enable setting the bias voltage to have a same value. Furthermore, it is possible to where the focal length is designated, enable the value of the bias voltage to be set to be large around the focal length and setting a distance range in which the bias voltage is large.

As described above, according to the present embodiment, the bias voltage is properly and variably controlled according to setting of various types of parameters in addition to an image mode corresponding to an ultrasound scanning mode, whereby an ultrasound image corresponding to the variable control of the bias voltage can be generated.

Also, according to the present embodiment, an ultrasound image with a favorable image quality can be generated and an ultrasound image with power saved can be generated according to the setting of the image mode and the parameters.

(Second Embodiment)

Next, a second embodiment of the present invention will be described with reference to FIG. 5. The ultrasound probe 2 illustrated in FIG. 2 is a mechanical scanning ultrasound probe, and in the present embodiment, an electronic scanning ultrasound probe 2B can be connected selectively and used in addition to the mechanical scanning ultrasound probe 2.

Figure 5:
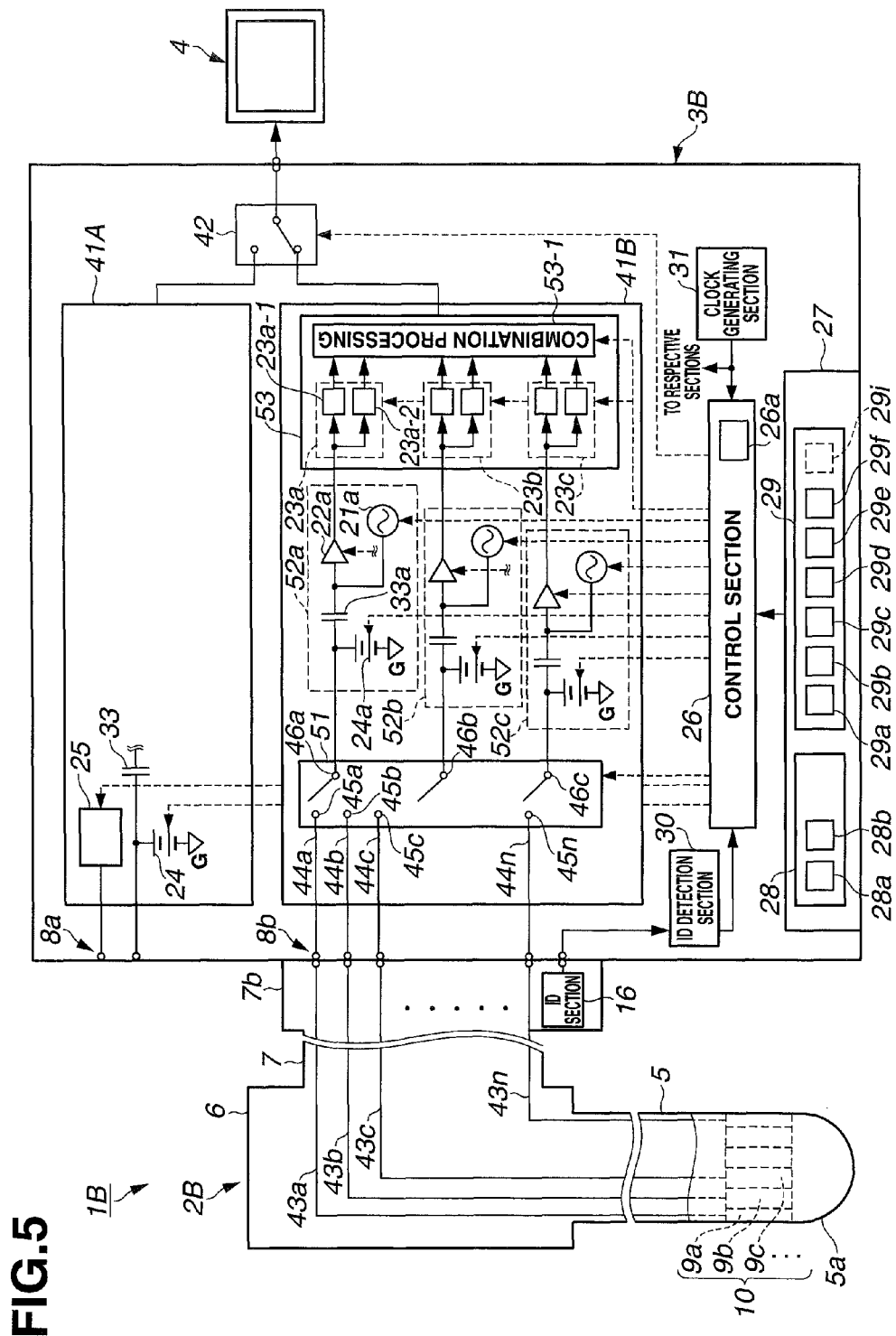
FIG. 5 is a diagram illustrating a configuration of an ultrasound diagnostic apparatus including a second embodiment of the present invention.

An ultrasound diagnostic apparatus 1B, which is illustrated in FIG. 5, includes an observation apparatus 3B including connector receivers 8a and 8b as connection portions to which a mechanical scanning ultrasound probe 2 or an electronic scanning ultrasound probe 2B is detachably connected.

The observation apparatus 3B includes a mechanical scanning processing section 41A electrically connected to the connector receiver 8a, an electronic scanning processing section 41B electrically connected to the connector receiver 8b, a switching section 42, a control section 26 and an operation section 27.

The mechanical scanning processing section 41A includes a drive signal generating section 25, a bias voltage outputting section 24, a transmit section 21, a capacitor 33, an amplifier 22 and a receive section 23, which has been described with reference to FIG. 2, (only a part thereof is illustrated in FIG. 5).

The electronic scanning ultrasound probe 2B, as in the mechanical scanning ultrasound probe 2, includes an elongated insertion portion 5 to be inserted into, e.g., a body cavity, a grasping portion 6 provided at a rear end of the insertion portion 5, the grasping portion 6 being grasped by an operator such as a surgeon, and a cable portion 7 extending from the grasping portion 6, and at an end portion of the cable portion 7, a connector 7b that is detachably connected to the connector receiver 8b of the observation apparatus 3B is provided.

At a distal end portion 5a of the insertion portion 5 of the ultrasound probe 2B, a C-MUT array 10a including a plurality of (for example, m) C-MUTs 9a, 9b, 9c, . . . 9n provided by forming a plurality of the above-described C-MUTs 9 into a strip-like shape and arranged along a cylindrical surface of the distal end portion 5a is disposed.

The C-MUTs $9i$ (i=a, b, . . . n) included in the C-MUT array 10 are connected to contact points in the connector 7b via signal wires $43i$ inserted in, e.g., the insertion portion 5.

The respective contact points connected to the signal wires $43i$ are connected to respective contact points 45i of a multiplexer 51 included in the electronic scanning processing section 41B in the observation apparatus 3B via signal wires $44i$ connected to respective contact points of the connector receiver 8b.

Here, the C-MUTs $9i$ may be provided with an acoustic lens 15 as illustrated in FIG. 2 or may be provided with no acoustic lens 15. Although the below description is provided supposing that no acoustic lens 15 is provided, even if an acoustic lens 15 is provided, use of electric focusing enables ultrasound to be focused at a focal length shorter than a focal length provided by the acoustic lens 15 or to be focused at a focal length longer than the focal length provided by the acoustic lens 15.

Also, for example, inside the connector 7b of the ultrasound probe 2B, an ID section 16 that generates identification information (ID) unique to the ultrasound probe 2B is provided. The ID generated by the ID section 16 is detected by an ID detection section 30 provided on the observation apparatus 3B side.

The control section 26 can identify characteristics of the C-MUT array 10 used in the ultrasound probe 2B and the C-MUTs $9i$ included in the C-MUT array 10 from the detected ID.

The electronic scanning processing section 41B includes the multiplexer 51, a plural number of (for example, three) transmit and amplifier sections $52j$ (j=a, b, c), the plural number being a predetermined number smaller than the total number m of devices, and a combination processing section 53. The number of transmit and amplifier sections $52j$ is not limited to a predetermined number, for example, three, and may be two or four or more.

The transmit and amplifier sections $52j$ include transmit sections $21j$, amplifiers $22j$, bias voltage outputting sections $24j$ and capacitors 33j. In FIG. 5, e.g., a transmit section $21a$ included in a transmit and amplifier section $52a$ is specifically indicated with a reference numeral provided thereto, and reference numerals are omitted for other transmit and amplifier sections $52b$ and $52c$ for simplicity.

Also, the combination processing section 53 includes receive circuits or receive sections (hereinafter, "receive sections" is used) $23j$ that perform receive processing on output signals amplified by the respective amplifiers $22j$, and a combination processing circuit 53-1 that performs combination processing on the output signals from the receive sections $23j$. The combination processing section 53 may be defined as a receive and combination processing section that includes receive sections, which may be receive circuits, and a combination processing section including a combination processing circuit.

Although in the case of the mechanical scanning ultrasound probe 2, the transmit section 21 and the receive section 23 are responsive to the B-mode only, in the present embodiment, in order to accept the electronic scanning ultrasound probe 2B, the transmit sections $21j$ and the receive section $23j$ are responsive to the B-mode and the Doppler mode.

The transmit sections $21j$ each has a function that generates (transmits) a B-mode transmit signal and a Doppler-mode transmit signal, and the receive sections $23j$ include B-mode processing sections $23j$-1 that generate a B-mode ultrasound image and Doppler processing sections $23j$-2 that generate a Doppler-mode ultrasound image of a moving observation object such as bloodstream using a Doppler phenomenon (also referred to as Doppler-mode ultrasound image or Doppler image).

In FIG. 5, a B-mode processing section $23a$-1 and a Doppler processing section $23a$-2 included in a receive section $23a$ are specifically provided with reference numerals, and reference numerals are omitted for other receive sections $23b$ and $23c$ for simplicity.

In the present embodiment, the control section 26 controls, e.g., the transmit section 21 in the mechanical scanning processing section 41A as in the first embodiment, and further controls the respective sections in the electronic scanning processing section 41B, based on designation and setting by the image mode setting section 28 and designation and setting of parameters by the parameter setting section 29 in the operation section 27.

More specifically, the control section 26 performs switching control of the multiplexer 51, control of the transmit sections 21j,the amplifiers 22j and the bias voltage outputting sections 24j included in the transmit and amplifier sections 52j, and control of the combination processing section 53. Also, the control section 26 controls operations of the B-mode processing sections 23j-1, the Doppler processing sections 23j-2 and the combination processing circuit 53-1 in the combination processing section 53 based on designation and setting from the operation section 27.

Furthermore, in the present embodiment, the image mode setting section 28 includes a Doppler mode setting section 28b for designating and setting the Doppler mode for displaying a Doppler image in the case of electronic scanning, in addition to a B-mode setting section 28a, which is provided in the first embodiment.

Furthermore, the control section 26 controls switching of the switching section 42. For example, where the mechanical scanning ultrasound probe 2 is connected to the observation apparatus 3B, the control section 26 performs control of switching so that a video signal processed by the mechanical scanning processing section 41A is outputted to a monitor 4. Meanwhile, where the electronic scanning ultrasound probe 2B is connected to the observation apparatus 3B, the control section 26 performs control of switching so that a video signal processed by the electronic scanning processing section 41B is outputted to the monitor 4. Where the operator designates and sets switching via the switching section 42 from the operation section 27, the control section 26 also performs control of the switching according to the designation and setting.

The multiplexer 51 is a multiplexer having a three-contact point switching function, which can selectively connect each of a plurality of, specifically, three switching contact points 46a, 46b and 46c to one of the m contact points 45i. The number of contact points is not limited to three, and the arrangement can be made to select the number of contact points, for example, around two to ten, according to the number of transmit and amplifier sections 52 provided. Also, within the number of transmit and amplifier sections 52 provided, the number of transmit and amplifier sections 52 actually used can be set.

The switching contact points 46j are connected to the transmit and amplifier sections 52j. The transmit and amplifier sections 52j apply transmit signals from the transmit sections 21j to the C-MUTs 9i included in the C-MUT array 10 via the multiplexer 51 to transmit ultrasound from the C-MUTs 9i,and receive reflected ultrasound and convert the reflected ultrasound into receive signals and amplify the receive signals by means of the amplifiers 22j and input the amplified receive signals to the combination processing section 53.

The control section 26 includes a timing control section 26a that controls timings (times) for outputting transmit signals from the three transmit sections 21a to 21c according to the designation and setting of a focal length parameter from the focal length parameter setting section 29c. For example, where transmit signals are applied from the transmit sections 21a,21b and 21c to the C-MUTs 9a, 9b and 9c, respectively, the timing control section 26a in the control section 26 controls the timing for outputting the transmit signals so that the transmit signals are outputted from the transmit sections 21a and 21c at timings a little before a timing for outputting the transmit signal from the transmit section 21b (which is set so as to correspond to the focal length).

As a result of controlling the timings for outputting the transmit signals as described above, ultrasound can be electrically focused at the designated and set focal length.

The combination processing section 53 combines, for example, output signals from the three receive sections 23a, 23b and 23c by means of, e.g., addition in the combination processing circuit 53-1, and a video signal outputted through the combination processing section 53 is outputted to the monitor 4 via the switching section 42.

Also, in the present embodiment, it is possible to make designation and setting to select the number of transmit and amplifier sections 52j used for ultrasound transmission and reception and the number of receive sections 23j in the combination processing section 53, which is, though, limited to the case of electronic scanning. In other words, the number of elements in the C-MUTs 9i driven almost simultaneously, that is, the number of elements in the C-MUTs 9i simultaneously used for generating one pixel when an ultrasound image is displayed can be selected. Thus, the parameter setting section 29 in the first embodiment is further provided with a device count parameter setting section 29f for designating and setting the number of C-MUT elements as the number of elements in the C-MUTs 9i for generating one pixel.

Then, where the number of elements is set to be small rather than a case where the number of elements is set to be large, the control section 26 performs control so that the bias voltage is set to be larger.

Figure 6:
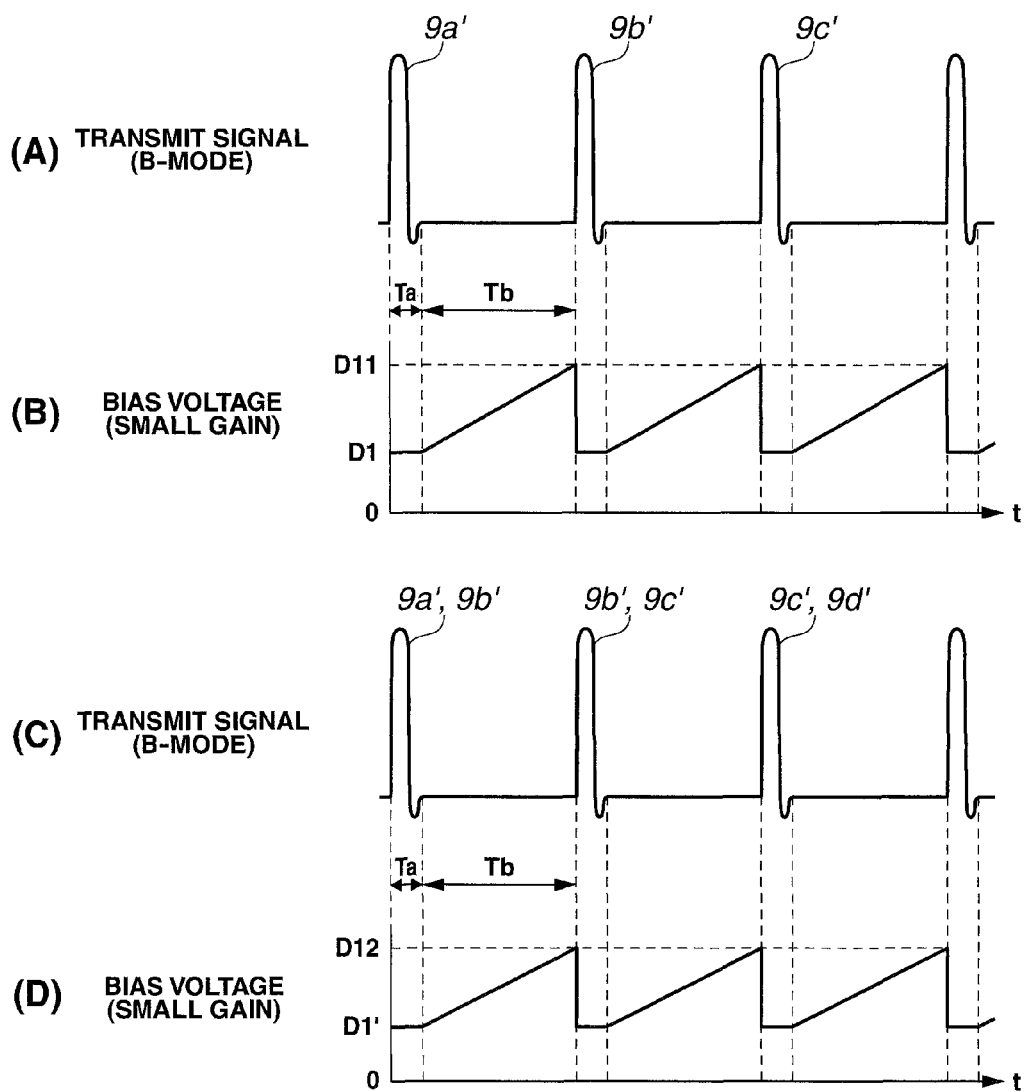
FIG. 6 includes diagrams illustrating example waveforms of transmit signals in electronic scanning and bias voltages set in synchronization with the transmit signals and according to device counts.

FIGS. 6(A) and 6(B) illustrate waveforms of transmit signals and bias voltages where only one transmit and amplifier section 52a is used for transmission and reception so as to drive sequentially each one of the C-MUTs. Reference numerals 9a', 9b' and 9c',... denote transmit signals from the C-MUTs 9a, 9b, 9c, ..., respectively.

FIGS. 6(C) and 6(D) illustrate waveforms of transmit signals and bias voltages where transmission and reception are performed by the two transmit and amplifier sections 52a and 52b in such a manner that two adjacent C-MUTs are driven simultaneously and the driven C-MUTs are sequentially switched from one another.

Where the number of elements is small, the amplitude of the transmit signal is small (compared to a case where the number of elements is large), and thus, the value of the bias voltage is increased in a receive period Tb compared to the case where the number of elements is large, to increase the sensitivity, enabling acquisition of an ultrasound image with a favorable image quality (provided, however, that the amplitude of the transmit signal remain constant even if the number of elements is changed).

More specifically, the control section 26 performs control so that a peak value D11 of the bias voltage where the number of elements is one, which is illustrated in FIG. 6(B), is larger than a peak value D12 of the bias voltage where the number of elements is two, which is illustrated in FIG. 6(D) (D11>D12). Here, FIGS. 6(B) and 6(D) indicate cases where a same gain is designated and set (for example, the gain is small).

In other words, the control section 26 performs control so that as the number of elements simultaneously driven increases, the value of the bias voltage decreases. Where the number of elements is large, the amplitude of the transmit signal can be made to be larger according to the number of elements, and thus the value of the bias voltage can be made to be small. In other words, the value of the bias voltage applied to one device can made to be relatively small, and thus, deterioration in characteristics due to application of high bias voltage can be reduced and the lifetime can be extended.

Also, as in the case of the bias voltage in the receive period Tb, a bias voltage D1' in a transmit period Ta in the case of FIG. 6(D) is one provided for a larger number of elements compared to the case of FIG. 6(B), and thus, the bias voltage D1' is set to be smaller than the bias voltage D1 in the transmit period Ta in the case of FIG. 6(B) (D1>D1'). The bias voltages D1 and D1' are set according to the size, the ultrasound characteristics and the device count of the C-MUTs 9i.

FIGS. 6(C) and 6(D) illustrate an example where two devices are driven simultaneously, and for example, where D1" is a bias voltage in a transmit period Ta when three devices are driven simultaneously, setting is made so that D1>D1'>D1". Also, where D12' is a peak value of the bias voltage in a receive period Tb when three devices are driven simultaneously, setting is made so that D11>D12>D12'.

In the present embodiment, where the B-mode is designated and set via the image mode setting section 28 when the electronic scanning ultrasound probe 2 is connected, variable control of the bias voltage by the control section 26 according to the designation and setting of parameters via the parameter setting section 29 is similar to the case where the mechanical scanning ultrasound probe 2B is used.

For example, where the gain is set to be small or large, the control section 26 variably controls the bias voltage as in FIG. 3(B) or 3(C). Also, where the display range is set to be small or large, the control section 26 variably controls the bias voltage as in FIG. 3(D) or 3(E). In this case, the transmit signal for mechanical scanning in FIG. 3(A) is substituted with, for example, the electronic scanning transmit signal in FIG. 6(A).

Furthermore, where the focal length according to electronic focusing is set to be small or large, the control section 26 variably controls the bias voltage as in FIG. 4(B) or 4(C). In this case, the transmit signal for mechanical scanning in FIG. 4(A) is substituted with transmit signals from a plurality of C-MUTs with varied output timings.

Figure 7:
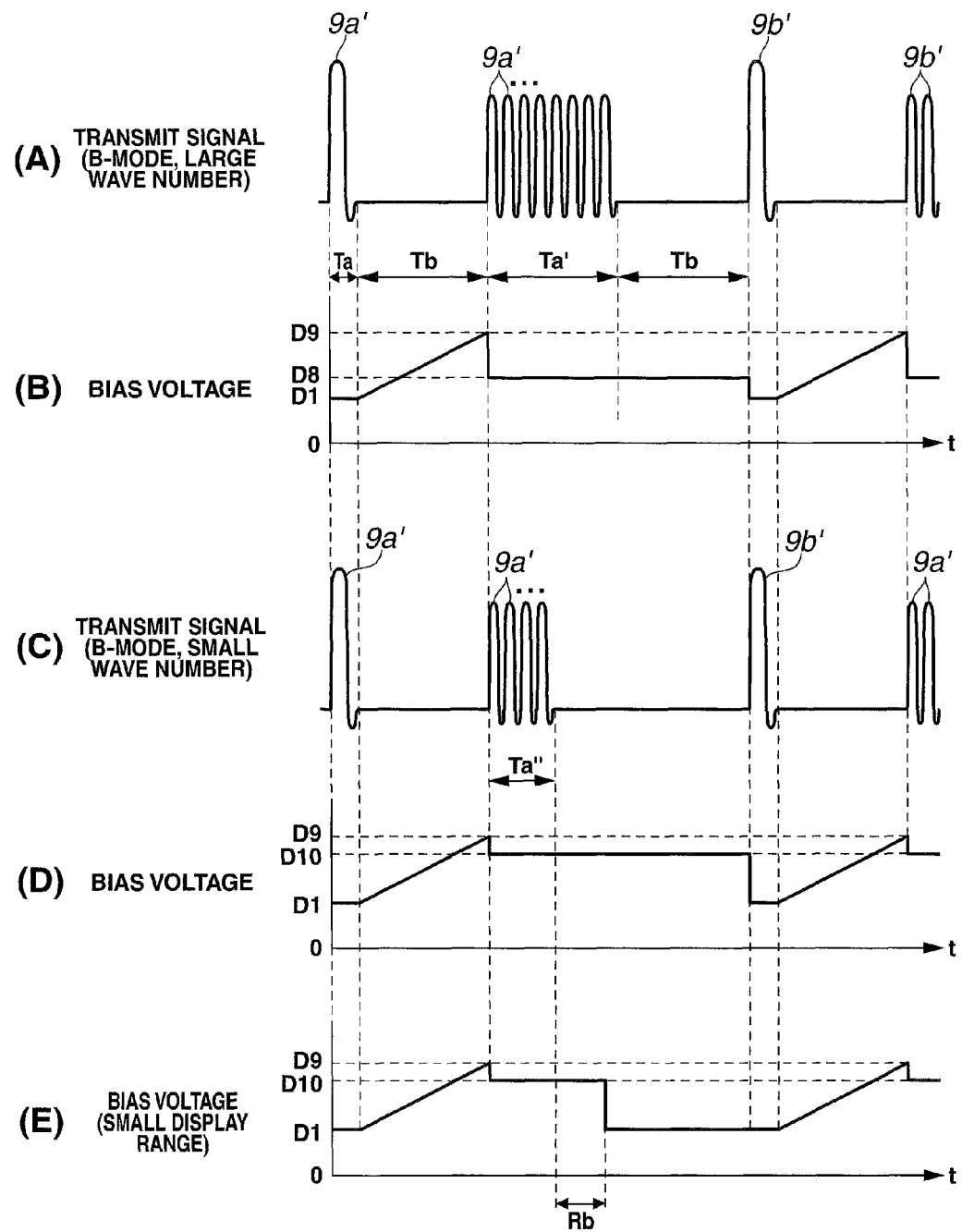
FIG. 7 includes diagrams illustrating example waveforms of B-mode transmit signals where a Doppler mode is selected and example waveforms of bias voltages variably set according to wavenumbers of the Doppler-mode transmit signals.

Also, where the electronic scanning ultrasound probe 2B is connected, the operator can also designate and set the Doppler mode via the Doppler mode setting section 28b provided in the image mode setting section 28.

Where the Doppler mode is designated and set, the control section 26 designates and sets a scanning mode with a combination of a B-mode transmit signal and a Doppler-mode transmit signal.

Where the Doppler mode is designated and set, the control section 26 performs control so that, for example, as illustrated in FIG. 7(A) or 7(C), the transmit section 21a outputs a B-mode transmit signal having a wavenumber of 1 and a Doppler-mode (burst waveform) transmit signal having a frequency that is the same as or different from that of the transmit signal and having a wavenumber of two or more, for example, alternately. The output is not limited to the alternate output, and may be controlled so that both are outputted in a predetermined cycle (like 1:2 or 2:1 where the output periods of the former and the latter are briefly represented by 1:1).

In FIG. 7(A) and 7(C), a transmit period for a Doppler-mode transmit signal is indicated by Ta' and Ta", respectively.

In synchronization with such transmit signal, the control section 26 performs controls so that the bias voltage outputting section 24 outputs the bias voltage as indicated in FIG. 7(B) or 7(D).

Here, FIGS. 7(A) and 7(B) and FIGS. 7(C) and 7(D) fall under a case where a burst waveform transmit signal having a large wavenumber is designated and set and a case where a burst waveform transmit signal having a small wavenumber is designated and set, respectively.

The transmit signal in FIG. 7(A) includes an electronic scanning transmit signal 9a' and a transmit signal 9a' having a wavenumber of eight resulting from eight repetitions of the transmit signal 9a' and a next transmit signal 9b' and a transmit signal 9b' having a wavenumber of eight resulting from eight repetitions of the transmit signal 9b'....

In the example illustrated in FIG. 7(A), for example, the burst waveform transmit signal 9a' having a wavenumber of eight is indicated as having a frequency higher than that of the transmit signal 9a' having a wavenumber of one; however, as described above, the burst waveform transmit signal 9a' may be set to have a frequency that is the same as that of the transmit signal 9a' having a wavenumber of one. The same applies to the case of FIG. 7(C) below.

Also, the transmit signal in FIG. 7(C) includes an electronic scanning transmit signal 9a' and a transmit signal 9a' having a wavenumber of four resulting from four repetitions of the transmit signal 9a', a next transmit signal 9b' and a transmit signal 9b' having a wavenumber of four resulting from four repetitions of the transmit signal 9b'...

In other words, the control section 26 variably controls the bias voltage according to the wavenumber parameter set for a case where the burst waveform transmit signal, which is a Doppler-mode transmit signal, has a large wavenumber or a case where the burst waveform transmit signal has a small wavenumber. More specifically, in B-mode receive periods Tb, the control section 26 controls the bias voltage so that the bias voltage is increased as in the case of FIG. 6(B) or 6(D) (the sensitivity is increased on the far side).

Meanwhile, in Doppler-mode receive periods Tb, the control section 26 performs control so that the bias voltage has a constant value with no temporal change as illustrated in FIG. 7(B) or 7(D), and also performs control so that a value D10 of the bias voltage in the case where the burst waveform transmit signal has a small wavenumber is larger than a value D8 of the bias voltage where the burst waveform transmit signal has a large wavenumber (D10>D8).

Although here, FIG. 7(A) illustrates a case of a large wavenumber where the burst waveform transmit signal has a wavenumber of eight and FIG. 7(C) illustrates a case of a small wavenumber where the burst waveform transmit signal has a wavenumber of four, the wavenumber values are not limited to those of these cases. Furthermore, the present invention is not limited to the cases where the B-mode transmit signal and the Doppler-mode transmit signal are alternately outputted as illustrated in FIGS. 7(A) and 7(C).

Furthermore, it is possible that: a part of an area included in a B-mode ultrasound image is designated, and a Doppler image is generated by a Doppler-mode transmit signal only for such part.

As can be seen from the FIGS. 7(B) and 7(D), even where the wavenumber of the burst waveform transmit signal is changed, the peak value D9 of the bias voltage is set to be the same in the B-mode receive periods Tb.

In the Doppler-mode receive periods Tb, the control section 26 performs control so that the bias voltage has a constant value with no temporal change as illustrated in FIG. 7(B) or 7(D). Furthermore, the control section 26 performs control so that the value of the bias voltage with no temporal change is larger in the case where the burst waveform transmit signal has a small wavenumber than in the case where the burst waveform transmit signal has a large wavenumber.

As described above, in the Doppler-mode receive periods Tb, the control section 26 performs control so that the bias voltage has a constant value with no temporal change as illustrated in FIG. 7(B) or 7(D), whereby when a change in frequency is detected, such detection can be made with high accuracy without, e.g., a signal width of a receive signal being affected by temporal change of the bias voltage.

Also, where the wavenumber is small, the value of the bias voltage is made to be larger than (that of the case where the number is large) to further increase the sensitivity of the C-MUT 9j for receive signal, and thus, frequency change can be detected as in the case where the wavenumber is large. Accordingly, a Doppler image (Doppler-mode ultrasound image) with a favorable image quality, which reflects movement of, e.g., bloodstream with good precision can be generated.

In the case of the Doppler mode, also, where, for example, a display range of a Doppler-mode ultrasound image is changed, the value of the bias voltage may be changed and set according to the display range.

For example, in the case of FIG. 7(C), where a display range of a Doppler-mode ultrasound image is set to be small, as illustrated in FIG. 7(E), control is performed so that the bias voltage has a large value (D10 in the illustrated example) only for a receive period Rb corresponding to the display range, and may be decreased (to, for example, D1) in a receive period Tb except the receive period Rb. Consequently, the bias voltage is made to be large only for the receive period Rb corresponding to the display range, ensuring a predetermined sensitivity, and enabling power saving and reduction in time in which the large bias voltage is applied to the C-MUTs 9j. Accordingly, characteristics change (or deterioration) due to application of a large bias voltage can be suppressed even in long-term use.

Although FIG. 7(E) illustrates a case of a display range close to the near field side, it is possible to enable designation and setting of a display range to be displayed as a Doppler image. In this case, control may be performed so that the bias voltage has a large value only for a receive period (corresponding to Rb above) corresponding to the designated and set display range.

Furthermore, where the control may be performed for the electronic scanning ultrasound probe 2B as described above, effects similar to those of the mechanical scanning ultrasound probe 2 described in the first embodiment are provided. Furthermore, where the Doppler mode is designated and set for the electronic scanning ultrasound probe 2B, the bias voltage is variably controlled properly responding to the Doppler-mode parameter setting according to the designation and setting, enabling generation of an ultrasound image with a favorable image quality.

As described above, the present embodiment enables use of any of the mechanical scanning ultrasound probe 2 and the electronic scanning ultrasound probe 2B, and the bias voltage is variably controlled according to setting of various parameters in addition to an image mode according to the ultrasound scanning mode to generate a favorable ultrasound image.

The above-described embodiments may be partially varied.

For example, in the second embodiment, the control section 26 controls the bias voltage to have a constant value in receive periods corresponding to a near field to a far field where the Doppler mode is designated and set, and variably controls the bias voltage to be increased from the near field toward the far field where the B-mode is designated and set from the image mode setting section; however, control may further be performed so that as the number of elements driven simultaneously in electronic scanning increases, the value of the bias voltage decreases.

Figure 8:
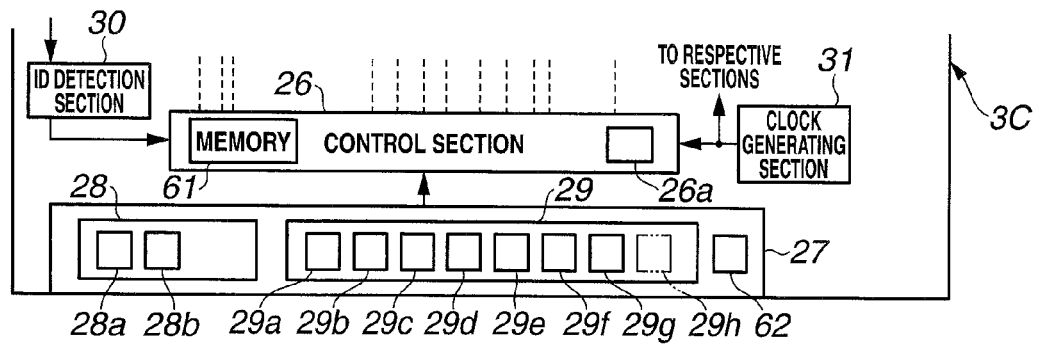
FIG. 8 is a diagram illustrating a part of an observation apparatus in a variation resulting from variation of a part of the configuration in FIG. 5.

Otherwise, it is possible to enable the control section 26 to variably control the bias voltage according to an ultrasound characteristic of a tissue to be observed using ultrasound, that is, a living tissue included in an organ or a living body site such as a diseased part in a body cavity to which ultrasound is transmitted. FIG. 8 illustrates a part of a configuration of an observation apparatus 3C according to a variation in which certain functions have been added to the control section 26 and the operation section 27 in FIG. 5 to respond to such case.

A parameter setting section 29, which is illustrated in FIG. 8, further includes a frequency parameter setting section 29g for designating and setting (or selecting and setting) a frequency of a transmit signal as a frequency parameter in the configuration of the parameter setting section 29 in FIG. 5.

Where a tissue to be observed using ultrasound is a living tissue, if the ultrasound (transmit signal) has a high frequency, attenuation of the ultrasound during propagation in the living tissue is large compared to a case where the ultrasound has a low frequency.

Thus, where a frequency of the ultrasound (transmit signal) is designated and set via the frequency parameter setting section 29g, the control section 26 performs control so that the bias voltage is made to be large when the frequency is high compared to a case where the frequency is low, (to compensate the attenuation).

In this case, the control section 26 may perform control so that as the distance increases, the bias voltage increases, and also perform control so that such tendency is more significant in the former case than in the latter case (more specifically, in the former case, the bias voltage is made to be more significantly larger as the distance is larger than in the latter case).

As a result of such control being performed, even if the frequency of the ultrasound (transmit signal) is changed, a bias voltage properly responding to (ultrasound attenuation caused according to) the frequency can automatically be set, and an ultrasound image with a favorable image quality, which enables, i.e., inspection or examination to be easily conducted, can be generated.

Furthermore, in the case of the B-mode or in the case of use in the Doppler mode, if the frequency of the ultrasound (transmit signal) can selectively be designated and set, in consideration of ultrasound characteristics of an organ or a living body site as a tissue to be observed in addition to the designated and set frequency of the ultrasound, the control section 26 may perform control to change and set the bias voltage according to the ultrasound characteristics of the organ or living body site.

In order to perform such control, as illustrated in FIG. 8, for example, the control section 26 includes a memory 61 inside as a storage section that stores in advance association data (for example, a table) in which a plurality of organs or a plurality of living body sites, which are tissues to be observed, and ultrasound characteristics of the respective organs or living tissues are associated with each other for each of a plurality of ultrasounds (transmit signals).

The memory 61 is not limited to be provided inside the control section 26 and may be provided outside the control section 26. In other words, it is only necessary that the control section 26 can refer to the association data stored in the memory 61. Also, for the memory 61, for example, a flash memory, which has a non-volatile property and is writable, may be used.

Furthermore, as illustrated in FIG. 8, the operation section 27 further includes an organ/site selecting section (or a selection section) 62 that selects or sets an organ or a living body site to be actually observed using ultrasound from the aforementioned plurality of organs and living body sites whose ultrasound characteristics have been recognized, in the configuration in FIG. 5. Function of the organ/site selecting section 62 that selects an organ or living body site may be included in an organ/site parameter setting section 29*h* (that sets an organ/site parameter) as indicated by an alternate long and two short dashes line inside the parameter setting section 29.

The control section 26 refers to the corresponding ultrasound characteristic according to the ultrasound characteristic of an organ or living body site actually selected or set by an operator and controls a bias voltage according to the ultrasound characteristic in synchronization with a transmit signal.

Thus, the memory 61 may store the above association data further in association with bias voltage. For example, where a used frequency is set, the control section 26 may read a corresponding value or a distance-related characteristic of a bias voltage from the memory 61 according to the value of the ultrasound characteristic of an organ or living body site to be observed at that frequency, and control the bias voltage using the read value or characteristic.

For example, control may be made so that as an attenuation ratio of a tissue to be observed as an ultrasound characteristic is larger, the bias voltage is made to be larger so as to compensate the attenuation of ultrasound.

With the configuration that performs the aforementioned control, when an operator simply selects or sets an organ or living body site to be actually inspected via the selection section 62 or the organ/site parameter setting section 29*h*, the control section 26 automatically controls the bias voltage in synchronization with the transmit signal and according to the ultrasound characteristic of the organ or living body site for a frequency of ultrasound (transmit signal) in the relevant case, enabling acquisition of an ultrasound image with a favorable image quality, which enables, i.e., inspection or examination to be easily conducted. Thus, an observation apparatus with good operability can be provided.

Although the present variation has been described in terms of an example in which the present variation has been applied to the second embodiment, the present variation may be applied to the first embodiment.

Furthermore, as described below, in the above-described embodiments, an increase in receive signal sensitivity by means of a bias voltage may be provided within an acceptable range of the bias voltage in priority to a gain increase by means of the amplifier 22 for designation and setting of a gain exceeding one for a receive signal.

More specifically, for example, as indicated by a dotted line inside the parameter setting section 29 in FIG. 2 or 5, a sensitivity priority setting section 29*i* for gain parameter is provided. The sensitivity priority setting section 29*i* may be provided outside the parameter setting section 29.

The sensitivity priority setting section 29*i* provides setting to make an increase in sensitivity by means of a bias voltage within an acceptable range in priority to designation and setting of a gain via the gain parameter setting section 29*a*. Where priority of sensitivity increase is designated and set by the sensitivity priority setting section 29*i*, the control section 26 prioritizes the sensitivity increase over the designation and setting of the gain, and performs gain control so that a shortfall for a set gain in the sensitivity increase by means of the bias voltage is covered by a gain increase by the amplifier 22.

Here, although gain and sensitivity are not equivalent concepts, for example, a characteristic of an increase in amplitude of a receive signal when a gain provided by the amplifier 22 is increased to not less than one and a characteristic of an increase in amplitude of a receive signal when a bias voltage is increased to increase the sensitivity are found out in advance. Then, gain-bias voltage information for associating gain values each of which provides a receive signal having a same amplitude as that in the case of the increase in the bias voltage and corresponding bias voltage values to be sensitivity values, with each other is stored in, for example, the respective ID section 16. The control section 26 performs gain control in which sensitivity is prioritized over designation and setting of a gain with reference to the gain-bias voltage information read from the ID section 16. A storage section that stores the gain-bias voltage information in association with IDs may be provided inside the observation apparatus 3 or 3B.

Figure 9:
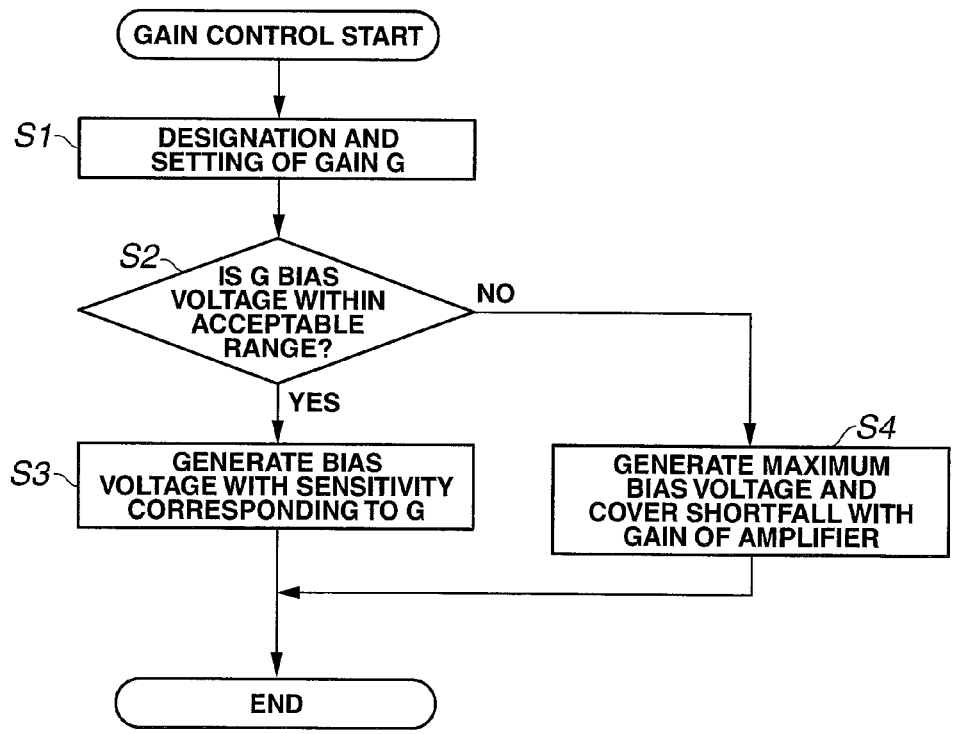
FIG. 9 is a flowchart illustrating contents of processing in gain control where sensitivity is prioritized over gain provided by an amplifier.

FIG. 9 illustrates an example of processing in the aforementioned gain control in which sensitivity is prioritized.

In step S1, a gain G for a receive signal is designated and set via the gain parameter setting section 29*a*. In step S2, the control section 26 determines whether or not the gain G can be covered by a sensitivity provided by a bias voltage within an acceptable range, with reference to the gain-bias voltage information.

In determination processing in step S2, if it is determined that the gain G can be covered by the sensitivity provided by a bias voltage, in step S3, the control section 26 performs control so that the bias voltage outputting section 24 outputs a bias voltage providing a sensitivity corresponding to the gain G.

Meanwhile, in the determination processing in step S2, if it is determined that the gain G cannot be covered by a sensitivity provided by a bias voltage, in step S4, the control section 26 performs control so that the bias voltage outputting section 24 outputs (generates) a maximum bias voltage within the acceptable range, and controls the gain of the amplifier 22 so that a shortfall in gain is covered by a gain increase by means of the amplifier 22.

As described above, it is more advantageous in terms of S/N ratio to increase the sensitivity of the C-MUT itself rather than to increase the gain provided by the amplifier 22.

Accordingly, the gain control as illustrated in FIG. 9 enables acquisition of an ultrasound image with an improved S/N ratio.

Furthermore, other embodiments resulting from e.g., the above-described embodiments or variations being partially combined fall under the present invention. For example, an observation apparatus that accepts the electronic scanning ultrasound probe 2B only can be configured from a part of the observation apparatus 3B according to the second embodiment that accepts an electronic scanning ultrasound probe 2B.

What is claimed is:

1. An ultrasound observation apparatus to which an ultrasound probe is connectable, the ultrasound probe including a capacitive micromachined ultrasound transducer whose sensitivity can be controlled according to an applied bias voltage, the ultrasound observation apparatus comprising:
    a transmit section that performs signal processing for outputting a transmit signal for causing the capacitive micromachined ultrasound transducer to transmit ultrasound, to the capacitive micromachined ultrasound transducer;
    a receive section that performs signal processing on a receive signal received by the capacitive micromachined ultrasound transducer, to display the receive signal as an ultrasound image;
    a bias voltage outputting section that variably outputs the bias voltage applied to the capacitive micromachined ultrasound transducer;
    an image mode setting section that designates and sets an image mode for displaying an ultrasound image corresponding to ultrasound scanning by the capacitive micromachined ultrasound transducer;

a parameter setting section that designates and sets a parameter for the signal processing on the transmit signal or the received receive signal;

an operation section including the image mode setting section and the parameter setting section, the operation section outputting a designation signal corresponding to the designation and setting of the image mode and the parameter; and a control section that controls the bias voltage based on the designation signal from the operation section, wherein the image mode setting section designates and sets a B-mode for imaging and displaying a luminance corresponding to a position and an amplitude of the receive signal or a Doppler mode for providing display as a Doppler image using a Doppler phenomenon;

wherein the parameter setting section designates and sets at least one of a gain for the receive signal, a display range for which the ultrasound image is displayed, a focal length for the ultrasound transmitted from the capacitive micromachined ultrasound transducer to be focused, a wavenumber of the transmit signal when the transmit signal is transmitted in the Doppler mode, a scanning type of the ultrasound probe, a number of the elements of the capacitive micromachined ultrasound transducers simultaneously driven if the ultrasound probe is an electronic scanning one, as a parameter; and wherein the control section controls the bias voltage in synchronization with the transmit signal and according to the designation and setting of image mode designated by the image mode setting section and the parameter by the parameter setting section; and wherein the control section controls the bias voltage so that the bias voltage has a constant value in a receive period in which a distance from the capacitive micromachined ultrasound transducer varies from a near field to a far field if the Doppler mode is designated and set, and variably controls a value of the bias voltage in the receive period so as to increase the value as the distance varies from the near field to the far field if the B-mode is designated and set by the image mode setting section.

2. The ultrasound observation apparatus according to claim 1, wherein if the Doppler mode is designated and set via the image mode setting section, the control section variably sets the bias voltage according to the designation and setting of the parameter of the wavenumber of the transmit signal from the parameter setting section.

3. The ultrasound observation apparatus according to claim 1, wherein if the Doppler mode is designated and set via the image mode setting section, the control section performs variable control so that as the wavenumber of the transmit signal according to the designation and setting of the parameter of the wavenumber of the transmit signal from the parameter setting section decreases, a value of the bias voltage in the receive period increases.

4. The ultrasound observation apparatus according to claim 3, wherein if the parameter of the focal length is designated and set via the parameter setting section, the control section performs control so that the value of the bias voltage is larger in a receive period corresponding to an area around the focal length including the focal length than in a receive period for an area except the area around the focal length.

5. The ultrasound observation apparatus according to claim 3, wherein the parameter setting section further designates and sets a frequency of the transmit signal as the parameter, and the control section variably controls the bias voltage in synchronization with the transmit signal and according to the designated and set frequency.

6. The ultrasound observation apparatus according to claim 5, further comprising a storage section that stores a plurality of organs or living body sites as tissues to be observed using ultrasound, and corresponding ultrasound characteristics in association with each other, wherein the operation section further includes a selection section that selects an organ or a living body site to be subjected to an actual ultrasound observation, and the control section variably controls the bias voltage in synchronization with the transmit signal and according to the ultrasound characteristic of the organ or the living body site selected by the selection section.

7. The ultrasound observation apparatus according to claim 5, wherein the control section performs variable control so that as the designated and set frequency is higher, the value of the bias voltage in the receive period increases.

8. The ultrasound observation apparatus according to claim 5, further comprising a first connection portion and a second connection portion to which a mechanical scanning ultrasound probe including the capacitive micromachined ultrasound transducer and an electronic scanning ultrasound probe including a plurality of the capacitive micromachined ultrasound transducers are selectively and detachably connected, wherein the transmit section includes a first transmit section that generates the transmit signal for the capacitive micromachined ultrasound transducer provided in the mechanical scanning ultrasound probe, and a second transmit section that generates the transmit signal for the plurality of the capacitive micromachined ultrasound transducers provided in the electronic scanning ultrasound probe; and wherein the receive section includes a first receive section that performs signal processing on the receive signal from the capacitive micromachined ultrasound transducer provided in the mechanical scanning ultrasound probe, and a second receive section that performs signal processing on the receive signal from the plurality of the capacitive micromachined ultrasound transducers provided in the electronic scanning ultrasound probe.

9. The ultrasound observation apparatus according to claim 8, wherein the second transmit section includes a predetermined number of transmit circuits that generate a predetermined number of transmit signals, the predetermined number of transmit signals being able to drive a predetermined number of capacitive micromachined ultrasound transducers simultaneously, the predetermined number being a number equal to or smaller than a total number of elements in the plurality of capacitive micromachined ultrasound transducers;

wherein the second receive section includes a predetermined number of receive circuits that enable simultaneous signal processing on a predetermined number of receive signals received by a predetermined number of capacitive micromachined ultrasound transducers, the predetermined number being a number equal to or smaller than the total number of elements in the plurality of capacitive micromachined ultrasound transducers.

10. The ultrasound observation apparatus according to claim 5, comprising a sensitivity priority setting section that if a gain exceeding one is designated and set for the receive signal, provides an increase in sensitivity by the bias voltage within an acceptable range of the bias voltage in priority to an increase in gain provided by an amplifier that amplifies the receive signal.

11. The ultrasound observation apparatus according to claim 3, wherein if a display range is designated and set, the control section performs variable control so that the value of the bias voltage is larger in a receive period corresponding to an area within the designated and set display range than in a receive period corresponding to an area outside the display range.

12. The ultrasound observation apparatus according to claim 1, wherein if the parameter of the focal length is designated and set via the parameter setting section, the control section performs control so that the value of the bias voltage is larger in a receive period corresponding to an area around the focal length including the focal length than in a receive period for an area except the area around the focal length.

13. The ultrasound observation apparatus according to claim 1, wherein the parameter setting section further designates and sets a frequency of the transmit signal as the parameter, and the control section variably controls the bias voltage in synchronization with the transmit signal and according to the designated and set frequency.

14. The ultrasound observation apparatus according to claim 1, comprising a sensitivity priority setting section that if a gain exceeding one is designated and set for the receive signal, provides an increase in sensitivity by the bias voltage within an acceptable range of the bias voltage in priority to an increase in gain provided by an amplifier that amplifies the receive signal.

* * * * *